US012725279B2

(12) United States Patent
Devani et al.

(10) Patent No.: US 12,725,279 B2
(45) Date of Patent: Sep. 1, 2026

(54) SYSTEMS AND METHODS FOR QUANTIFYING PHYSIOLOGIC TREMORS FOR HEALTH INSIGHTS VIA MOBILE DEVICES

(71) Applicant: BioTrillion, Inc., San Francisco, CA (US)

(72) Inventors: Savan R. Devani, San Francisco, CA (US); Juan Beron, San Francisco, CA (US); Derrick Mo, San Francisco, CA (US)

(73) Assignee: BIOTRILLION, INC., San Francisco, CA (US)

( * ) Notice: Subject to any disclaimer, the term of this patent is extended or adjusted under 35 U.S.C. 154(b) by 426 days.

(21) Appl. No.: 18/113,489

(22) Filed: Feb. 23, 2023

(65) Prior Publication Data

US 2023/0274445 A1 Aug. 31, 2023

Related U.S. Application Data

(60) Provisional application No. 63/314,134, filed on Feb. 25, 2022.

(51) Int. Cl.
*G06T 7/246* (2017.01)
*A61B 5/11* (2006.01)
(Continued)

(52) U.S. Cl.
CPC ............ *G06T 7/246* (2017.01); *A61B 5/1101* (2013.01); *G06T 7/60* (2013.01); *G06V 40/171* (2022.01);
(Continued)

(58) Field of Classification Search
CPC ......... G06T 7/246; G06T 7/60; G06T 7/0016; G06T 2207/30004; G06T 2207/30201;
(Continued)

(56) References Cited

U.S. PATENT DOCUMENTS 9,967,530 B2 * 5/2018 Bowen ................. H04N 9/3185
10,614,303 B2 * 4/2020 Klingström ............... G06T 7/13
(Continued)

FOREIGN PATENT DOCUMENTS

CN 111199165 A * 5/2020 ........... G06T 7/0002
WO WO-2020157746 A1 * 8/2020 ............. G06F 3/013
WO WO-2021195316 A1 * 9/2021 ........... A61B 5/1101

OTHER PUBLICATIONS

Guoen Cai, Zhirong Lin, Houde Dai, Xuke Xia, Yongsheng Xiong, Shi-Jinn Horng, Tim C. Lueth, Quantitative assessment of parkinsonian tremor based on a linear acceleration extraction algorithm, Biomedical Signal Processing and Control, vol. 42, 2018, pp. 53-62, ISSN 1746-8094, https://doi.org/10.1016/j.bspc.2018.01.008.
(Continued)

*Primary Examiner* — Henok Shiferaw
(74) *Attorney, Agent, or Firm* — Nixon Peabody LLP

(57) ABSTRACT

A system for generating an involuntary movement-based biomarker includes an imaging device configured to generate image data associated with a user, and a control system communicatively coupled to the imaging device. The control system is configured to identify, in a first image, a feature of the user, determine, in the first image, a first location parameter associated with the feature, and identify, in a second image, the feature of the user, and determine, in the second image, a second location parameter associated with the feature. The control system is further configured to calculate, based on a difference between the first location parameter and the second location parameter relative to a reference element present in the first and second images that is separate from the feature, a movement of the feature of the user, and generate, using the movement of the feature of the user, the movement-based biomarker.

20 Claims, 9 Drawing Sheets

(51) Int. Cl.
*G06T 7/60* (2017.01)
*G06V 40/16* (2022.01)

(52) U.S. Cl.
CPC ............... *G06T 2207/20056* (2013.01); *G06T 2207/20081* (2013.01); *G06T 2207/30041* (2013.01)

(58) Field of Classification Search
CPC . G06T 2207/20056; G06T 2207/20081; G06T 2207/30041; A61B 5/1128; A61B 5/1114; A61B 5/4082; A61B 5/165; A61B 5/4863; A61B 5/6898; A61B 5/7257; A61B 5/1101; G06V 10/82; G06V 40/171
See application file for complete search history.

(56) References Cited

U.S. PATENT DOCUMENTS

| | | | | |
|---|---|---|---|---|
| 11,109,015 | B2 * | 8/2021 | Iwasaki | H04N 13/398 |
| 2010/0092049 | A1 * | 4/2010 | Schroeder | A61B 3/113 382/128 |
| 2018/0210546 | A1 * | 7/2018 | Rawlinson | G06V 40/193 |
| 2020/0251190 | A1 * | 8/2020 | Glasner | A61B 5/0022 |
| 2020/0364868 | A1 * | 11/2020 | Zhang | G06T 7/248 |
| 2021/0233663 | A1 * | 7/2021 | Nazem | G16H 50/20 |
| 2022/0058822 | A1 * | 2/2022 | Naruniec | G06N 3/0442 |
| 2022/0114838 | A1 * | 4/2022 | Xu | G06V 10/761 |
| 2022/0222897 | A1 * | 7/2022 | Yang | G06V 40/16 |
| 2023/0245271 | A1 * | 8/2023 | Song | G06V 40/171 382/284 |
| 2023/0326016 | A1 * | 10/2023 | Zhang | G06V 10/764 382/128 |
| 2024/0021317 | A1 * | 1/2024 | Hood | G16H 50/30 |
| 2024/0420290 | A1 * | 12/2024 | Vatanparvar | A61B 5/0077 |

OTHER PUBLICATIONS

Ferenčík, N.; Jaščur, M.; Bundzel, M.; Cavallo, F. The Rehapiano—Detecting, Measuring, and Analyzing Action Tremor Using Strain Gauges. *Sensors* 2020, 20, 663. The Rehapiano—Detecting, Measuring, and Analyzing Action Tremor Using Strain Gauges.

Bazgir O, Habibi SAH, Palma L, Pierleoni P, Nafees S. A classification system for assessment and home monitoring of tremor in patients with Parkinson's disease. J Med Signals Sens. 2018;8(2):65, 10.4103/jmss.JMSS_50_17.

Wang, X., Garg, S., Tran, S.N. et al. Hand tremor detection in videos with cluttered background using neural network based approaches. *Health Inf Sci Syst* 9, 30 (2021). https://doi.org/10.1007/s13755-021-00159-3.

* cited by examiner

SYSTEMS AND METHODS FOR QUANTIFYING PHYSIOLOGIC TREMORS FOR HEALTH INSIGHTS VIA MOBILE DEVICES

This application claims the benefit of U.S. Provisional Application No. 63/314,134, filed Feb. 25, 2022, the disclosure of each of which is hereby incorporated by reference herein in its entirety.

TECHNICAL FIELD

Background

Tremor (in many anatomic features) is a physiological condition that can be indicative of a person's health status. Traditionally, tremor has been subjectively assessed, however, when attempts to quantitively measure tremor, the primary sensor modality used has been mechanical, for example, by inertial measurement units (IMUs). While it is possible to measure mechanically, most devices carried by people are not designed to measure movements associated with tremor. For example, mechanical measurement devices (e.g., IMUs) are not designed to measure small and directionally oscillating motion, or frequently directionally changing motion, or may not be able to contact the anatomic feature of tremor (e.g. eyes). Accordingly, a need exists for improved systems and devices for measuring tremor.

BRIEF DESCRIPTION OF THE DRAWINGS

Disclosed herein are embodiments of systems, apparatuses, and methods pertaining generating movement-based biomarkers. This description includes drawings, wherein.

Figure 1:
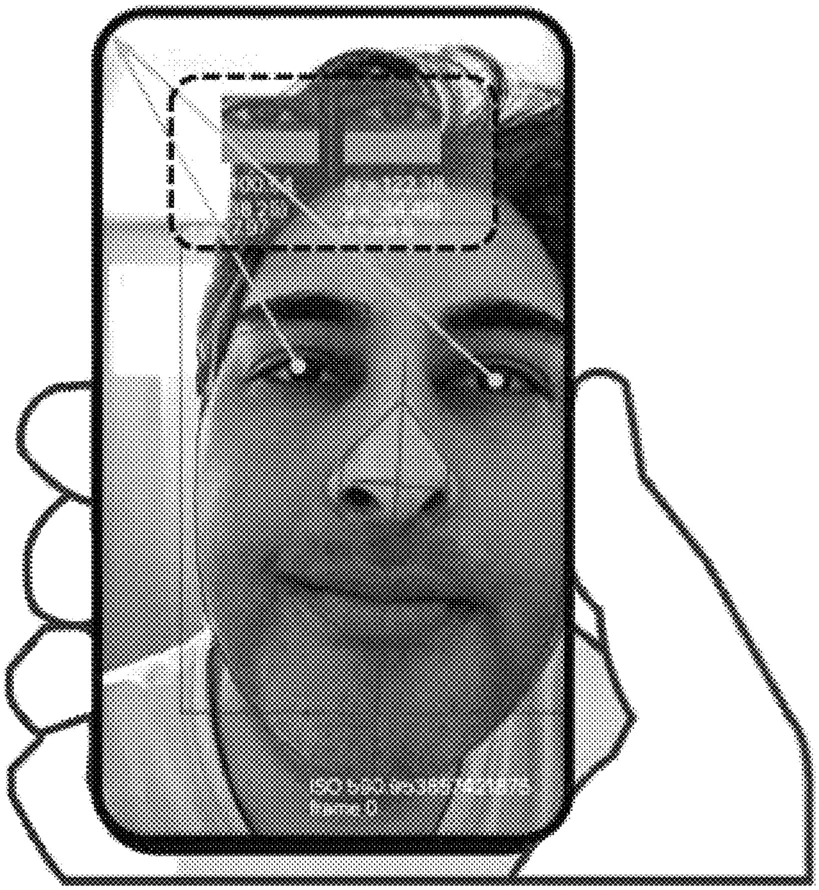
FIG. 1 depicts a user capturing image data via a mobile device, according to some embodiments.
Figure 2A:
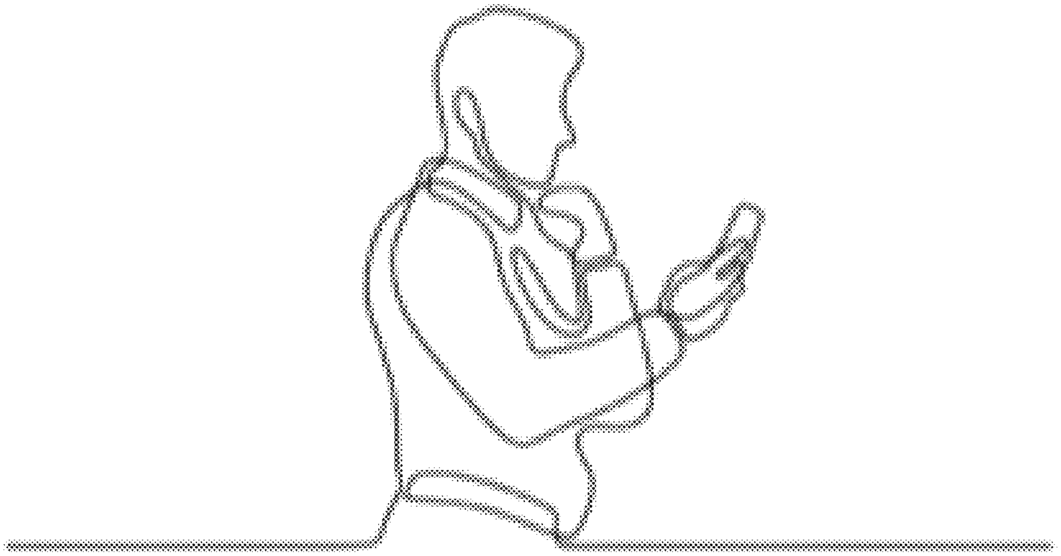
FIG. 2A depicts a user capturing image data via a mobile device, according to some embodiments.
Figure 2B:
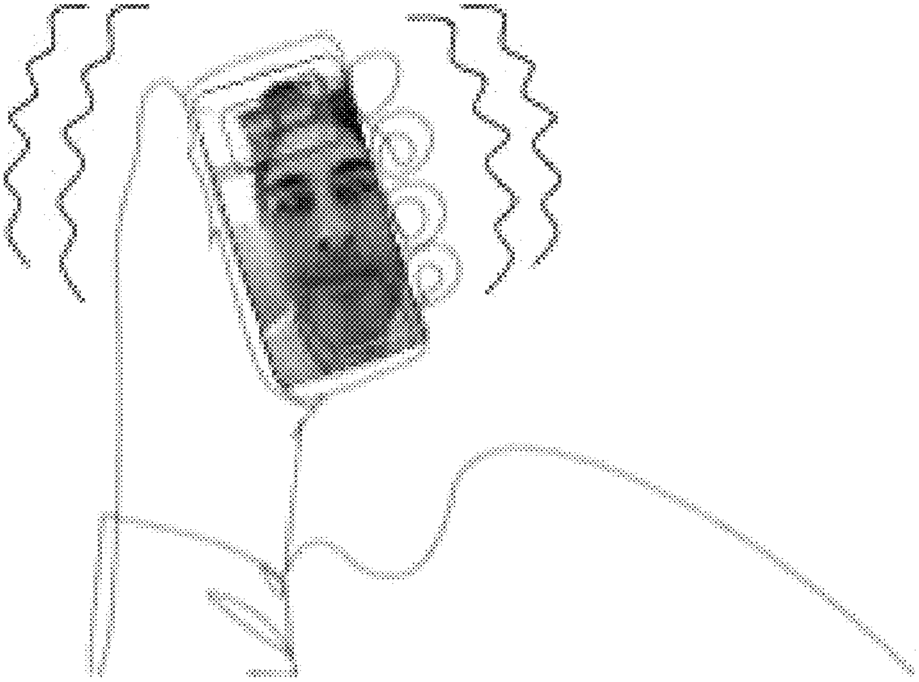
FIG. 2B depicts movement of a user's hand while capture image data via a mobile device, according to some embodiments.
Figure 3:
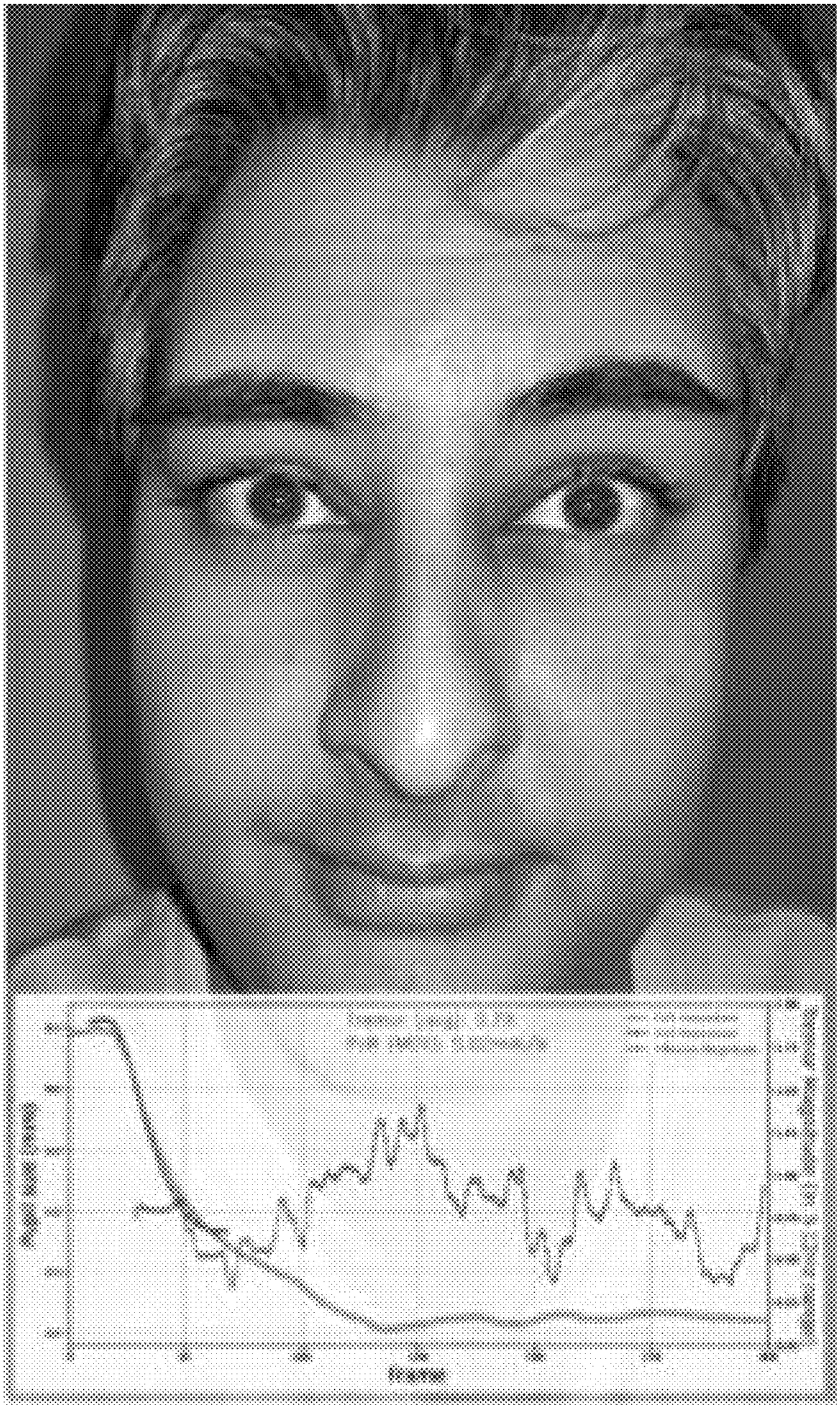
FIG. 3 depicts movement data associated with image data captured, according to some embodiments.
Figure 4:
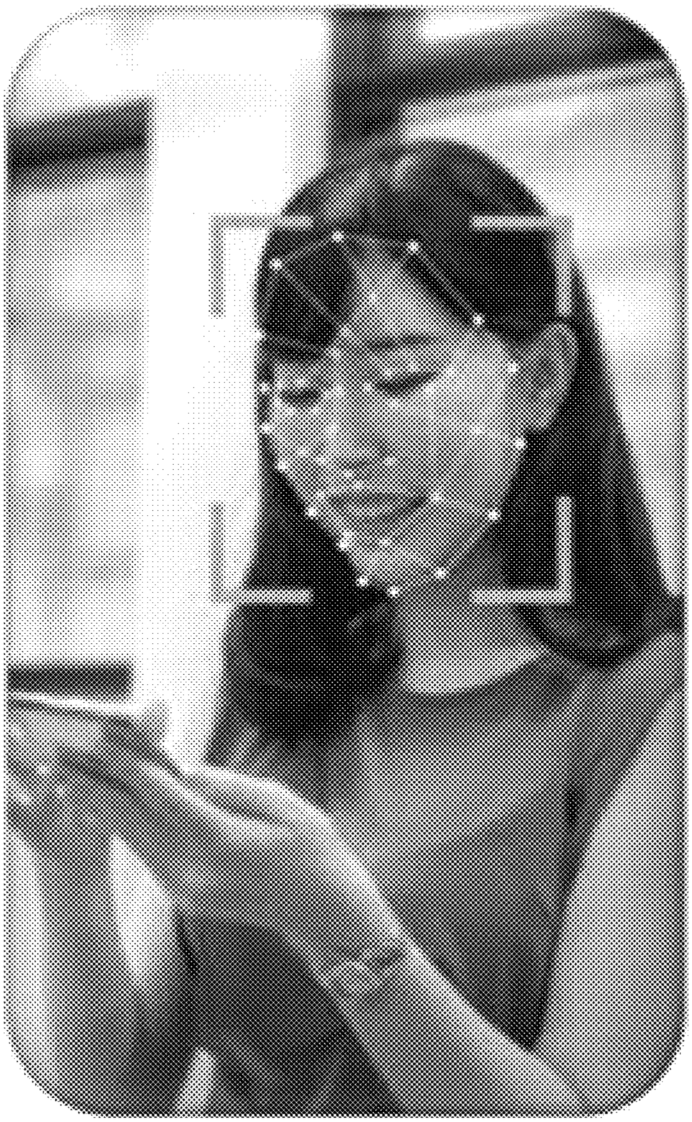
FIG. 4 depicts features of a user, according to some embodiments.
Figure 5:
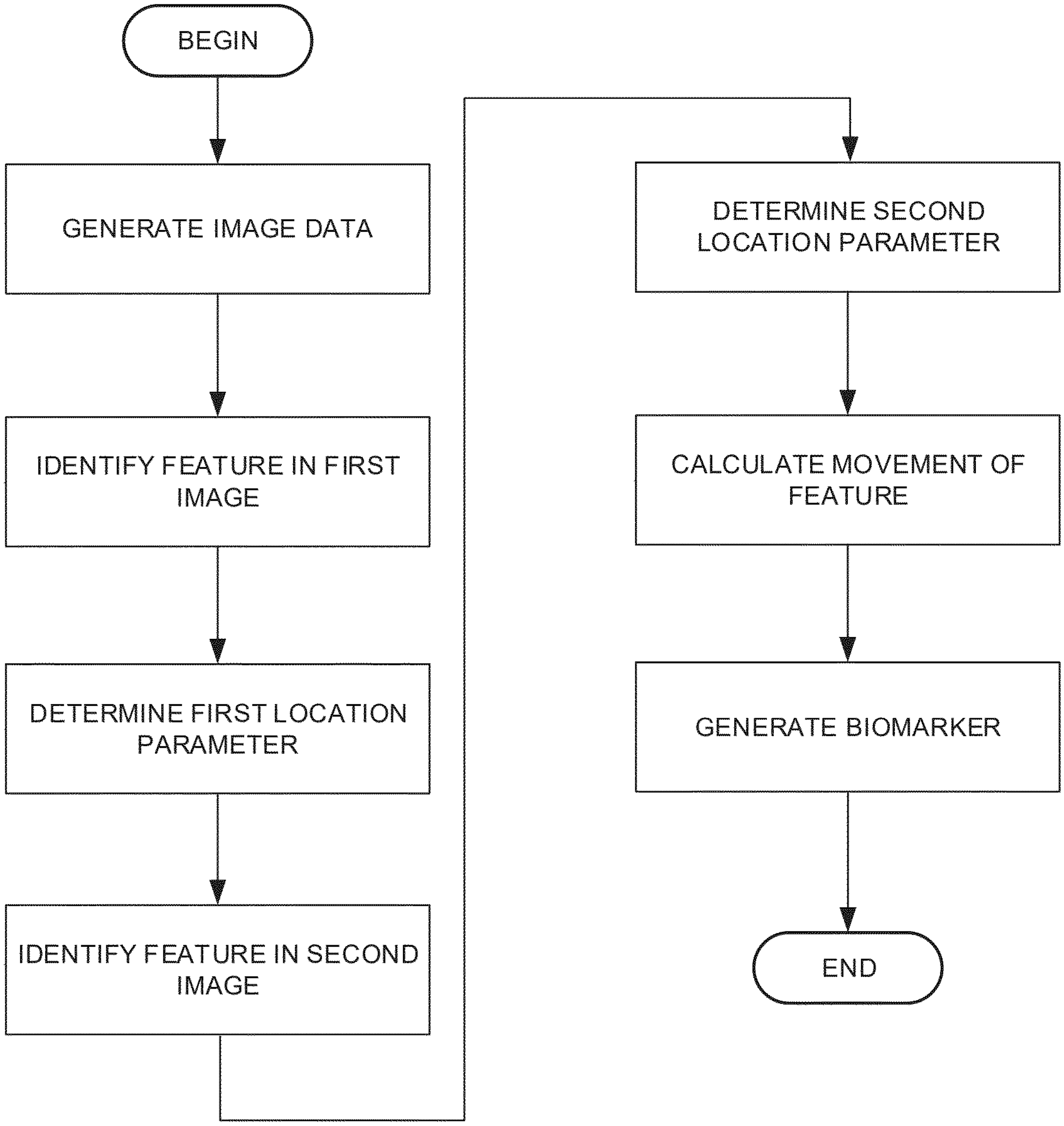
FIG. 5 is a flow chart depicting example operations for generating movement-based biomarkers, according to some embodiments.
Figure 6:
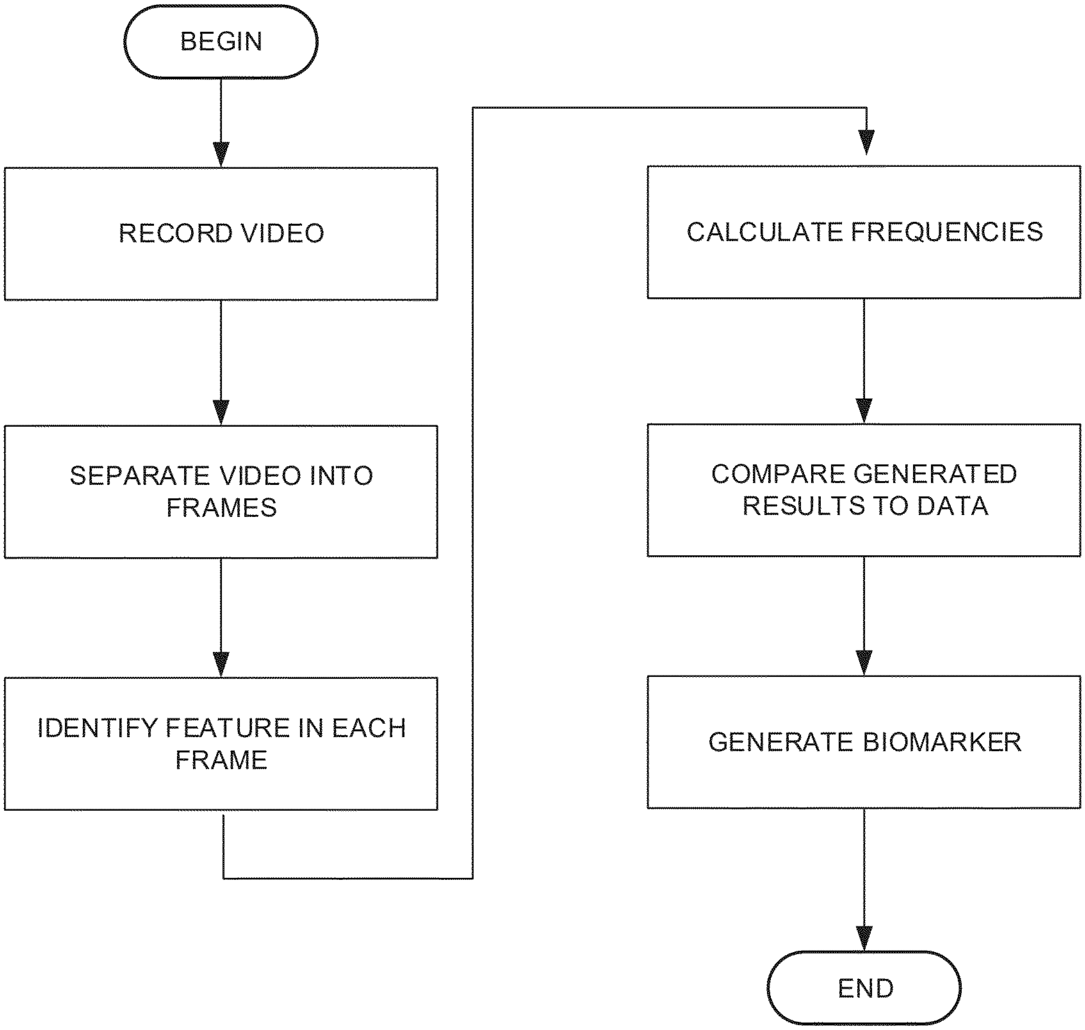
FIG. 6 is a flow chart depicted example operations for generating a biomarker, according to some embodiments.

Elements in the figures are illustrated for simplicity and clarity and have not necessarily been drawn to scale. For example, the dimensions and/or relative positioning of some of the elements in the figures may be exaggerated relative to other elements to help illustrate understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

Generally speaking, pursuant to various embodiments, systems, apparatuses, and methods are provided herein useful to generating biomarkers. In some embodiments, a system for generating a movement-based biomarker comprises an imaging device configured to generate image data associated with a user, the image data being reproducible as a series of visually readable images including a first image and a second image, or consecutive series of images, a control system communicatively coupled to the imaging device, the control system configured to identify, in the first image, a feature of the user, determine, in the first image, a first location parameter associated with the feature of the user, identify, in the second image, the feature of the user, determine, in the second image, a second location parameter associated with the feature of the user, calculate, based on the first location parameter associated with the feature of the user and the second location parameter associated with the feature of the user, movement of the feature of the user, and generate, using the movement of the feature of the user, the movement-based biomarker. In some embodiments, measurements are taken indirectly (e.g., optically), as indirect measurements can be more accurate and precise due to the optical modality not being limited by the mechanical approaches, inertia, particularly vulnerable to small and directionally oscillating movement. These systems, methods, and apparatuses can be used to measure both hand tremor or eye tremor, based on the center of the eyes (iris or pupil) relative to a primary reference point being either, for example, the corner/border of the display frame (e.g. hand tremor) or a precisely trackable location on the face (e.g. eye tremor). Additionally, the benefit of optically measuring tremor is its ability to be contactless.

Tremor is a physiological condition that has traditionally been measured mechanically (e.g. via inertial motion units, accelerometers, gyroscopes). These mechanical measurements are not optimal for measuring tremor. For instance, IMU sensors (accelerometer and gyro) are typically most accurate when measuring long kinetic vectors, but lose accuracy when dealing with micro kinetic vectors (e.g. hand or eye tremors).

Described herein are systems, methods, and apparatus that seek to overcome these disadvantages by measuring tremor based on image data (i.e., optically). Such optical and indirect measurements can be more accurate and precise due to the optical modality not being limited by the mechanical approaches, inertia, particularly vulnerable to small and directionally oscillating movement.

This invention can also combine other application programming interfaces (APIs) that developed by third party vendors to improve the quality of biomarkers generated. For example, ARKit, an augmented reality tool kit developed by Apple Inc. for its iOS developers to use in the iOS ecosystem, can be a useful aid to measure the micro-distance instability vectors from the center of an image, while an image/picture is being taken. ARKit also allows a user to point his/her camera at 1 edge of a table and tilt or move the phone camera to the other edge of the table in the view finder and calculates the width of the table. In the same manner, this should allow the algorithm to calculate unintentional instability intra-pic taking (by turning off the iPhone's built-in image stabilizer and then calculate the length of those tremor vectors and either use them to bolster the accuracy of the IMU/kinetic sensors, or supplant them. These measures would be another type of digital biomarker (e.g. quantified hand tremor or eye tremor) that can be tracked by our technology for acute or longitudinally progressive neurologic diseases (e.g. Parkinson's). These measures of this digital biomarker (or the features of it is composed of) can also be passively generated. For example, the regular tracking and monitoring can be done whenever a user's face is captured by any video recording device (e.g. smartphone, headsets) and the application can use the data obtained to calculate and store on the side as meta data that goes in the App.

Another benefit of optically measured micro kinetics, as opposed to mechanically measured, is its ability to be contactless. For example, the eye is a delicate anatomic region of the eye where it would not be feasible to connect to a mechanical IMU. Such an example would be saccades, which are known as quick, simultaneous movement of both eyes between two or more phases of fixation in the same direction. Saccades are typically signs of a neurologic disorder. The same systems, methods, and apparatuses can be used to measure saccades, with the only difference being the primary reference point changing from the corner/border of the display frame to an anatomic location on the head that small enough that its location can be objectively determined and/or precisely tracked across images frames, such as centers of pupils or irises in the eyes and the inner and outer canthus' (corner of the eye where the upper and lower eyelids meet) on the face or other facial landmarks such as the corners of the mouth, the tip of the nose, and the chin ("precise facial landmarks").

Tremor, particularly in the hands or eyes, is a well-studied phenomenon in both academic and clinical settings. It is one of the few physiological signs that can be objectively measured, in contrast to the preponderance of subjective behavioral assessments, making it a valuable tool in detecting or diagnosing conditions and diseases associated with it. According to the National Institute of Neurological Disorders and Stroke (NIH), there are more than 20 different types of tremors that can affect different parts of the body, including the hands and eyes. These types of tremors have the following major classifications: essential tremor, dystonic tremor, cerebellar tremor, psychogenic tremor, physiologic tremor, enhanced physiologic tremor, parkinsonian tremor, and orthostatic tremor.

Many of the tremor types listed above can be caused by a variety of physiological conditions or diseases, such as anxiety, stroke, traumatic brain injury, multiple sclerosis, nystagmus, and other neurodegenerative diseases like Parkinson's disease. Moreover, tremor can be a useful factor in differentiating between neurodegenerative diseases, such as Alzheimer's disease (which is more cognitive in nature) and Parkinson's disease (which is more motor-related).

With the improved tracking and detecting power of classical and deep learning models, BioEngine4D is capable of separating measures of motion oscillating in different frequency zones (e.g. separating signal from tremor in the hand or eye from noise caused by motion in the body or head). For the remaining part of this section, we will discuss three example use cases of this invention, also known as hand tremor (or "hTremor") and eye tremor (or "iTremor") (digital biomarkers in "BioEngine4D"), deployed using only a contemporary smartphone already owned by over 3 billion global humans: Disease detection, anxiety or panic detection, and panic disorder detection. This is only a partial list of what BioEngine4D's digital biomarkers are capable of potentially detecting and monitoring, among many other potentially commercial or clinical use cases.

Parkinson's Disease:

Based on the research published by Parkinson's Foundation, approximately 60,000 Americans are diagnosed with Parkinson's Disease (PD) each year and there are more than 10 million people worldwide living with this disease. The number of PD patients are expected to rise at an exponential rate due to the accelerating speed of aging population and current lack of preventive or detective healthcare innovations in the healthcare community.

Traditionally, diagnosis of PD is made by a physician or neurologist based on the presence of two out of four main symptoms over a period of time. One of those symptoms is tremor and its presence is determined during an examination by a neurologist. The decision to report to a physician the presence of tremor depends on the tremor's severity and an early detection of abnormal tremor can be difficult since the tremor can be subtle.

Early detection of PD could facilitate earlier clinically confirmatory diagnoses and interventions, potentially slowing down the progression of the disease and reducing its symptoms with appropriate treatments. A tool owned by over 1B people that could identify the presence of abnormal tremor over a period of time, would provide great commercial convenience, access, and affordability.

Anxiety or Panic:

Based on the research published by Anxiety & Depression Association of America (ADAA), anxiety is affecting 40 million adults, or 18.1% of the population every year in the United States. With constantly increasing exposures to direct and indirect media platforms and growing complexities of societal rules, today's generation is more likely to suffer from anxiety compared to their previous generations. Anxiety disorders are a group of psychological conditions whose key features include excessive anxiety, fear, worry, avoidance, and compulsive rituals, and produce or result in inordinate morbidity, overutilization of healthcare services, and functional impairment. These disorders are among the most prevalent psychiatric conditions in the United States; women are more likely than men to experience anxiety disorders. Anxiety disorders listed in the Diagnostic and Statistical Manual of Mental Disorders ($4^{th}$ Ed., The American Psychiatric Association, Washington, D.C., U.S.A., 1994, pp. 393 to 444), include panic disorder with and without agoraphobia, agoraphobia without history of panic disorder, specific phobia, social phobia, obsessive-compulsive disorder (OCD), post-traumatic stress disorder (PTSD), acute stress disorder, generalized anxiety disorder (GAD), anxiety disorder due to a general medical condition, substance-induced anxiety disorder, and specific phobias.

Nystagmus:

Nystagmus is a neurological disorder that affects the way the eyes move. It is characterized by involuntary, rhythmic eye movements that can be rapid, jerky, or oscillatory in nature. Nystagmus can be caused by a variety of underlying conditions, including congenital abnormalities, head injuries, certain medications, and neurological disorders such as multiple sclerosis.

Nystagmus can cause a variety of visual symptoms, including blurred vision, double vision, and difficulty reading or tracking moving objects. In severe cases, it can also cause dizziness and loss of balance. Treatment for nystagmus typically focuses on managing the underlying condition that is causing the eye movements, although some people may benefit from vision therapy or medication.

A tool that could accurately track and measure eye movements could be useful for individuals living with nystagmus and their healthcare providers. This tool could help to provide a more objective and precise measurement of the severity of nystagmus, which could in turn help to guide treatment decisions and improve outcomes. The tool would need to be non-invasive, easy to use, and accurate in order to be effective for individuals with nystagmus.

Using Optical Flows:

Most applications of the optical modality have to do with the image generation or measure of the target of the generated image. Rarely do we use the optical modality (of any device) to glean information about the source of the generated image—in this case a user and their own hand. A set of optical flows is determined from a video with the help of some digital video processing technique such as a deep neural network. Each optical flow includes a gray-scale image where the value of the pixel represents the intensity of the movement of that pixel. The set of optical flows is then processed by an autoencoder (e.g. a trained deep neural network) to obtain a movement-based biomarker that could be in some cases the strength of a type of tremor. This autoencoder can be trained in different ways to improve its accuracy. The publication includes different examples of ways to train the autoencoder: label discriminator, adversarial discrimination, with a reconstruction network, with synthetic data from the reconstruction network.

BioEngine4D is capable of extracting the location of elements of the human face that are small enough that its location can be objectively determined and/or precisely tracked across images frames. Elements such as the nose or ears have a subjective location since it depends on their definition or the angle of the face. On the other hand, elements such as the centers of pupils or irises in the eyes and the inner and outer canthus' (corner of the eye where the upper and lower eyelids meet) on the face or other facial landmarks such as the corners of the mouth, the tip of the nose, and/or the chin ("precise facial landmarks"), are easier to define which makes its true location more precise, consistently trackable over time or images, and robust to different angles at which the image could have been taken. For example, BioEngine4D can infer the location of the center of the pupils and irises ($LeftPUPIL_{center}$, $RightPUPIL_{center}$, $LeftIRIS_{center}$, $RightIRIS_{center}$) from a reasonable quality video that can be recorded from a wide range of consumer-facing recording devices. The users were instructed to be as still as possible while holding the recording device and looking at the camera in those videos.

Based on the correct implementations of these instructions, BioEngine4D is able to track the locations of the pupils and irises ($LeftPUPIL_{center}$, $RightPUPIL_{center}$, $LeftIRIS_{center}$, $RightIRIS_{center}$) and calculate the movement. The dynamics of pupils and irises' location are associated with involuntary movement from the hand holding the phone (e.g. image corner/border) relative to the eyes in the field of view (e.g. centers of the pupil and iris (x2) given these features are infinitesimally discrete down to a specific pixel, thus maximizing precision via consistency on a frame by frame basis). Based on the frequency of the movement, it can be categorized as involuntary tremor.

In other words, the model is able to infer hand (or eye) tremor without optically viewing the hand. The inference of four pixel points in the image (2 pupils and irises centers) provides additional confirmatory/redundancies that maximize the probabilistic likeliness of a motion vector being accurate and thus reducing noise related to the final measure. The inference of four points in the image (pupils and irises) helps reduce noise related with the prediction.

An alternative method to get the highest probabilistic accuracy is to infer tremor using each reference points individually (e.g. left pupil center), resulting in 4 measures, eliminating the measure with the highest variance from the mean, and then taking the mean of the resulting 3.

To determine the strength of the tremor, we analyze the change of the location of the pupils and irises ($LeftPUPIL_{center}$, $RightPUPIL_{center}$, $LeftIRIS_{center}$, $RightIRIS_{center}$) over time in the desired frequency domain following standard procedures used previously for tremor analysis.

The locations of the pupils and irises are given by the x, y, z coordinates. To transform these values in one signal that represents the movement of the pupils and irises, the mean value of the coordinates is calculated by obtaining one value from each pupil and iris. Based on the four resulting signals, the mean value at each moment in time is computed which results in a time series with only one value per frame.

The resulting time series is transformed to the frequency domain with the Fast Fourier Transform (FFT).

BioEngine4D's "hTremor" digital biomarker focuses on the frequencies that are specific to involuntary hand motion of a particular condition or disease (e.g. between 3 Hz to 12 Hz for Parkinson's based on consensus in clinical literature).

There are different metrics that can be used to assess the intensity of the signal relative to a frequency band. BioEngine4D's "hTremor" digital biomarker signal separation is based on the following formula:

$$\text{metric} = \sum_{i=f_1}^{f_2} S(i)$$

Which resembles an approximation of the signal power. $f_1 f_1$ and $f_2$ are the frequencies that define the frequency band, S(f) is the power spectral density or the squared magnitude of the FFT divided by $N^2$ (N is the number of elements in the time series) of the signal of interest. For our application related with PD, and $f_2$ are, in one embodiment, 3 and 12 Hz, respectively. These ranges can differ and be set dynamically based on different associated diseases.

This metric will indicate the magnitude of motion, within a specified frequency range (e.g. 3-12 Hz), of the user's hand holding the smartphone relative to the eye (iris or pupil). Through this method it is possible to obtain a tremor value for each video. If the user performs the same procedure at points through the day between stressors or acute events (e.g. stress, drug) or at specified times during the day on a longer longitudinal basis, the model is able to analyze the trends which can be a valuable digital biomarker for many clinically or commercial applications related to PD.

A user records a video that captures his/her face. The user is instructed to take a video selfie by holding the phone as motionless as possible, without any support from the head to fingers, for a short period of time (e.g. 3-5 seconds) increasingly the likeliness of motionless compliance. The video is processed by the smartphone where the location of the pupils and irises' center are inferred.

The location of the pupils and irises are transformed to the frequency domain. The metric for tremor is calculated base on the frequency domain analysis.

One single value is returned for the recorded video. The user should repeat this process over time to see the evolution of tremor and monitor if there is a substantial increase over time.

Once BioEngine4D has obtained the pupils and irises' locations from videos of users, BioEngine4D is able to identify, analyze and track the relation between detected tremor and the movements of the pupils by extracting these observations in the frequency domain with the help of Fast Fourier Transform. Since users are told to remain as still as possible, the tremor detected must be related to involuntary tremor. The inference of the pupil as well as the needed calculations to estimate the tremor can be achieved entirely in a consumer-facing recording devices such as smart-phones.

The metrics obtained from the model will indicate the amount of tremor that a person exhibits in the videos. Through this method it is possible to obtain a tremor value for each video. If the users perform the same procedure on a regular time interval, the model is able to analyze the trends which can be a valuable digital biomarker for an early detection of PD. The computer vision assessment allows the model to infer hand tremor without optically viewing or physically touching the hand and without using any traditional mechanical tremor detectors which are vulnerable to inertia-based noise.

The proposed method does not require that the user wears any device in contrast to mechanical methods. Additionally, since tremor is being calculated optically, then there is a significantly mitigated loss of accuracy for small movements which mechanical accelerometers are susceptible to due to their inertia and dependence on inferring motion from gravitational forces.

Fast Fourier Transform (FFT) Method

An important metric in spectral analysis is the signal power in a frequency band which is calculated as $$\int_{f_1}^{f_2} S(f)df$$

$f_1$ and $f_2$ are the frequencies that define the frequency band, S(f) is the power spectral density or the squared magnitude of the FFT divided by $N^2$ (Nis the number of elements in the time series) of the signal of interest. For our application, and example range for $f_1$ and $f_2$ are 3 and 12 Hz respectively.

The algorithm uses a metric that resembles an approximation of the signal power $$\text{metric} = \sum_{i=f_1}^{f_2} S(i)$$

The main difference of this metric and the signal power is that it should be multiplied by the size of the interval which is equal to sampling frequency divided by N. This will make an approximation of integral by rectangles.

The units of the power spectral density are the original units of the signal of interest squared divided by Hz [2].

Two types of signals of interest have been considered:

Following the procedure from, the signal of interest is the average movement in each direction $$s(t) = \frac{x(t) + y(t)}{2}$$

The second type defines the signal of interest as the magnitude of the movement.

$$s(t) = \sqrt{(x(t) - x(t-1))^2 + (y(t) - y(t-1))^2}$$

Alternative Method

This method counts the number of critical points of the signal that are located in a local minimum or maximum. This is equivalent to the number of times the signal's first derivative changes signs.

For the application, the algorithm has, the algorithm has two signals which are the x and y coordinates of the pupil. Each time a change in sign of the first derivative of any of the two signals is located the counter will increase by one. If a critical point is located for the same frame then the counter will increase by $\sqrt{2}$ Once the counting procedure is finished, the counter value is divided by the length of the signal in seconds to obtain the number of oscillations in a second (i.e., frequency in Hz). The counter value can also be used to estimate the magnitude of the tremor, with a higher value indicating a more severe tremor.

Figure 7:
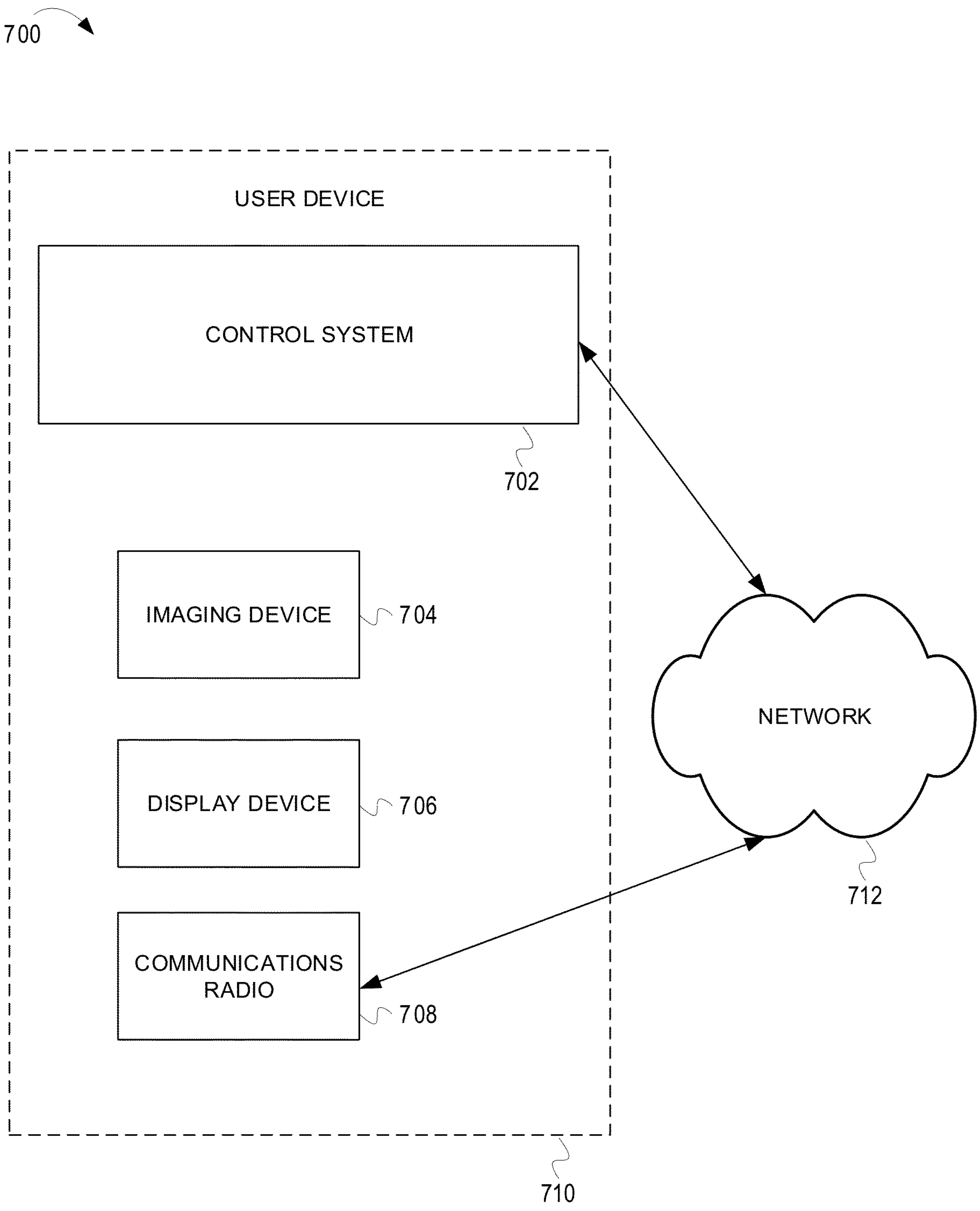
FIG. 7 is a block diagram of a system for generating movement-based biomarkers, according to some embodiments.
Figure 8:
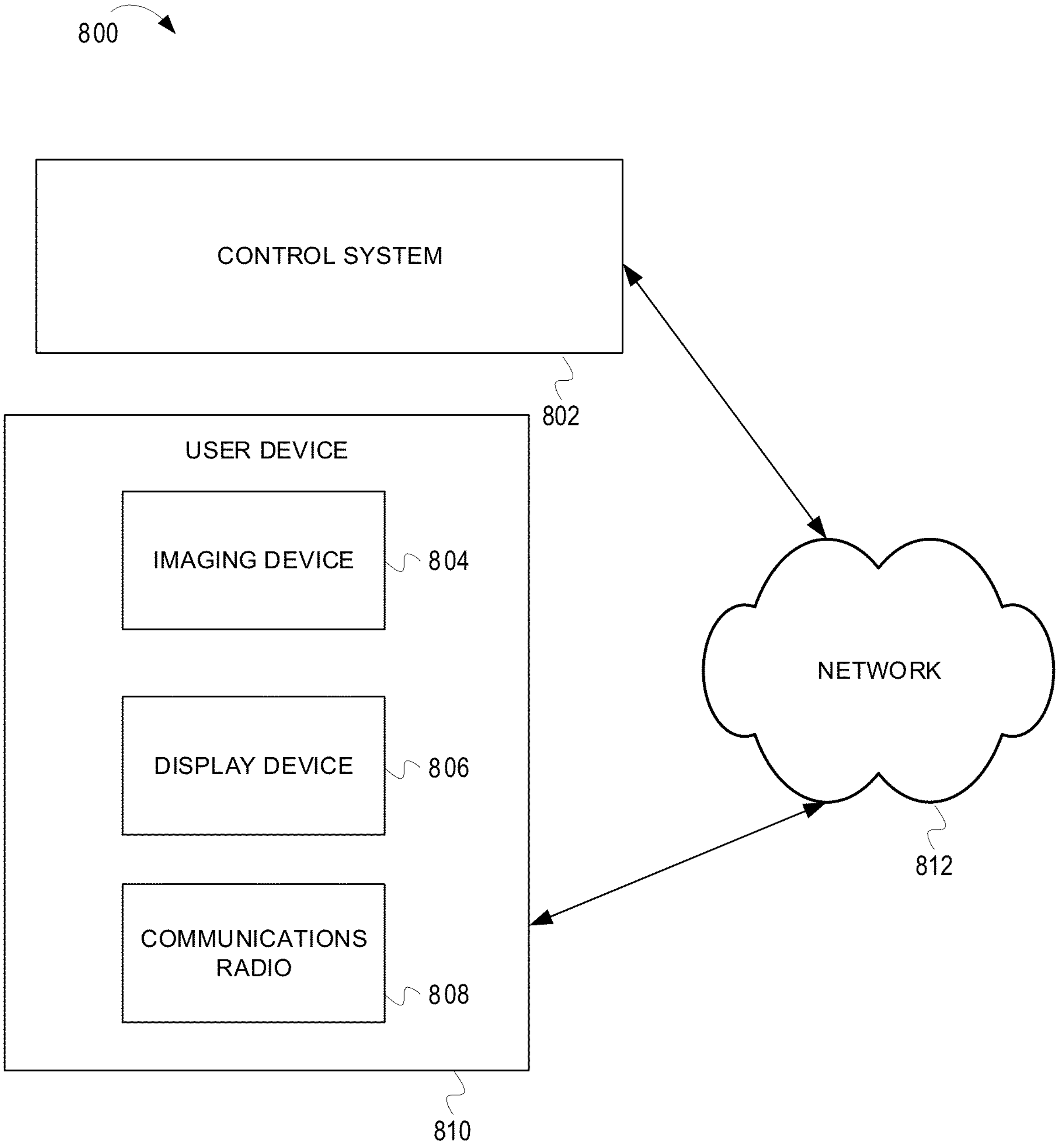
FIG. 8 is a block diagram of a system for generating movement-based biomarkers, according to some embodiments.
Figure 9:
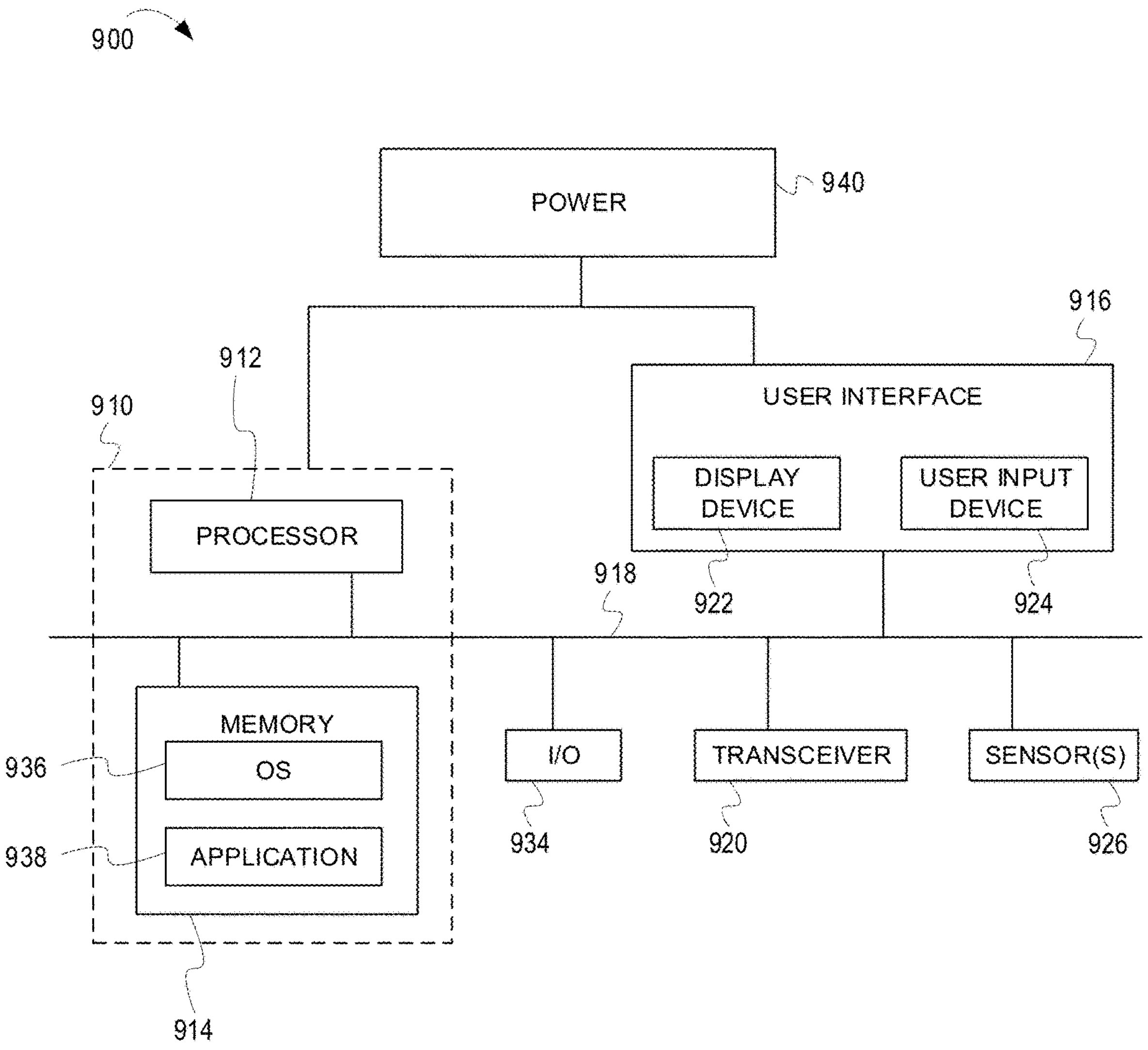
FIG. 9 is a block diagram of a system 900 that may be used for implementing any of the components, circuits, circuitry, systems, functionality, apparatuses, processes, or devices of the system of FIG. 7 or the system of FIG. 8, and/or other above or below mentioned systems or devices, or parts of such circuits, circuitry, functionality, systems, apparatuses, processes, or devices, according to some embodiments.

FIG. 8 is a block diagram of a system 900 that may be used for implementing any of the components, circuits, circuitry, systems, functionality, apparatuses, processes, or devices of the system 700 of FIG. 7 or the system 800 of FIG. 8, and/or other above or below mentioned systems or devices, or parts of such circuits, circuitry, functionality, systems, apparatuses, processes, or devices, according to some embodiments. The circuits, circuitry, systems, devices, processes, methods, techniques, functionality, services, servers, sources and the like described herein may be utilized, implemented and/or run on many different types of devices and/or systems. For example, the system 900 may be used to implement some or all of the control system, the user device, the input systems, the external systems, one or more of the databases, and/or other such components, circuitry, functionality and/or devices. However, the use of the system 900 or any portion thereof is certainly not required.

By way of example, the system 900 may comprise a processor (e.g., a control system) 912, memory 914, and one or more communication links, paths, buses or the like 918. Some embodiments may include one or more user interfaces 916, and/or one or more internal and/or external power sources or supplies 940. The processor 912 can be implemented through one or more processors, microprocessors, central processing unit, logic, local digital storage, firmware, software, and/or other control hardware and/or software, and may be used to execute or assist in executing the steps of the processes, methods, functionality and techniques described herein, and control various communications, decisions, programs, content, listings, services, interfaces, logging, reporting, etc. Further, in some embodiments, the processor 912 can be part of control circuitry and/or a control system 910, which may be implemented through one or more processors with access to one or more memory 914 that can store commands, instructions, code and the like that is implemented by the control system and/or processors to implement intended functionality. In some applications, the control system and/or memory may be distributed over a communications network (e.g., LAN, WAN, the Internet) providing distributed and/or redundant processing and functionality. Again, the system 900 may be used to implement one or more of the above or below, or parts of, components, circuits, systems, processes and the like.

In one embodiment, the memory 914 stores data and executable code, such as an operating system 936 and an application 938. The application 938 is configured to be executed by the user device 900 (e.g., by the processor 912). The application 938 can be a dedicated application (e.g., an application dedicated to the generation of biomarkers) and/or a general purpose application (e.g., a camera application, a photo application, etc.). Additionally, though only a single instance of the application 938 is depicted in FIG. 8, such is not required and the single instance of the application 938 is shown in an effort not to obfuscate the figures. Accordingly, the application 938 is representative of all types of applications resident on the user device (e.g., software preinstalled by the manufacturer of the user device, software installed by an end user, etc.). In one embodiment, the application 938 operates in concert with the operating system 936 when executed by the processor 912 to cause actions to be performed by the user device 900. For example, with respect to the disclosure contained herein, execution of the application 938 by the processor 912 causes the user device to perform actions consistent with the generation of biomarkers as described herein.

The user interface 916 can allow a user to interact with the system 900 and receive information through the system. In some instances, the user interface 916 includes a display device 922 and/or one or more user input device 924, such as buttons, touch screen, track ball, keyboard, mouse, etc., which can be part of or wired or wirelessly coupled with the system 900. Typically, the system 900 further includes one or more communication interfaces, ports, transceivers 920 and the like allowing the system 900 to communicate over a communication bus, a distributed computer and/or communication network (e.g., a local area network (LAN), wide area network (WAN) such as the Internet, etc.), communication link 918, other networks or communication channels with other devices and/or other such communications or combination of two or more of such communication methods. Further the transceiver 920 can be configured for wired, wireless, optical, fiber optical cable, satellite, or other such communication configurations or combinations of two or more of such communications. Some embodiments include one or more input/output (I/O) ports 934 that allow one or more devices to couple with the system 900. The I/O ports can be substantially any relevant port or combinations of ports, such as but not limited to USB, Ethernet, or other such ports. The I/O interface 934 can be configured to allow wired and/or wireless communication coupling to external components. For example, the I/O interface can provide wired communication and/or wireless communication (e.g., Wi-Fi, Bluetooth, cellular, RF, and/or other such wireless communication), and in some instances may include any known wired and/or wireless interfacing device, circuit and/or connecting device, such as but not limited to one or more transmitters, receivers, transceivers, or combination of two or more of such devices.

In some embodiments, the system may include one or more sensors 926 to provide information to the system and/or sensor information that is communicated to another component, such as the central control system, a delivery vehicle, etc. The sensors 926 can include substantially any relevant sensor, such as distance measurement sensors (e.g., optical units, sound/ultrasound units, etc.), optical-based scanning sensors to sense and read optical patterns (e.g., bar codes), radio frequency identification (RFID) tag reader sensors capable of reading RFID tags in proximity to the sensor, imaging system and/or camera, other such sensors or a combination of two or more of such sensor systems. The foregoing examples are intended to be illustrative and are not intended to convey an exhaustive listing of all possible sensors. Instead, it will be understood that these teachings will accommodate sensing any of a wide variety of circumstances in a given application setting.

The system 900 comprises an example of a control and/or processor-based system with the processor 912. Again, the processor 912 can be implemented through one or more processors, controllers, central processing units, logic, software and the like. Further, in some implementations the processor 912 may provide multiprocessor functionality.

The memory 914, which can be accessed by the processor 912, typically includes one or more processor-readable and/or computer-readable media accessed by at least the control system, and can include volatile and/or nonvolatile media, such as RAM, ROM, EEPROM, flash memory and/or other memory technology. Further, the memory 914 is shown as internal to the control system 910; however, the memory 914 can be internal, external or a combination of internal and external memory. Similarly, some, or all, of the memory 914 can be internal, external or a combination of internal and external memory of the processor 912. The external memory can be substantially any relevant memory such as, but not limited to, solid-state storage devices or drives, hard drive, one or more of universal serial bus (USB) stick or drive, flash memory secure digital (SD) card, other memory cards, and other such memory or combinations of two or more of such memory, and some or all of the memory may be distributed at multiple locations over a computer network. The memory 914 can store code, software, executables, scripts, data, content, lists, programming, programs, log or history data, user information, customer information, product information, and the like. While FIG. 8 illustrates the various components being coupled together via a bus, it is understood that the various components may actually be coupled to the control system and/or one or more other components directly.

Those skilled in the art will recognize that a wide variety of other modifications, alterations, and combinations can also be made with respect to the above described embodiments without departing from the scope of the disclosure, and that such modifications, alterations, and combinations are to be viewed as being within the ambit of the inventive concept.

What is claimed is:

1. A system for generating an involuntary movement-based biomarker, the system comprising:
- an imaging device configured to generate image data associated with a user, the image data being reproducible as a series of visually readable images including a first image and a second image;
- a control system communicatively coupled to the imaging device, the control system configured to:
  - identify, in the first image, a feature of the user;
  - determine, in the first image, a first location parameter associated with the feature of the user;
  - identify, in the second image, the feature of the user;
  - determine, in the second image, a second location parameter associated with the feature of the user;
  - calculate, based on a difference between the first location parameter associated with the feature of the user and the second location parameter associated with the feature of the user relative to a reference element present in the first and second images that is separate from the feature, a movement of the feature of the user, wherein the control system utilizes a tracking module configured to estimate micro-distance instability vectors for the movement, and wherein a built-in image stabilizer of the imaging device is disabled during generation of the image data; and generate, using the movement of the feature of the user, the movement-based biomarker.

2. The system of claim 1, wherein the feature of the user is associated with an eye of the user.

3. The system of claim 1, wherein the first location parameter is based on one of:

a distance from the feature of the user to a boundary of the first image; and a distance from the feature of the user to a reference point on a head or face of the user.

4. The system of claim 1, wherein the first location parameter is based on a coordinate system.

5. The system of claim 1, wherein the first location parameter associated with the feature of the user is associated with a pixel in the first image.

6. The system of claim 1, wherein the movement-based biomarker is associated with a health status of the user, and comprises at least one of tremor frequency, tremor amplitude, and a composite tremor score.

7. The system of claim 6, wherein the health status of the user further includes one or more of essential tremor, dystonic tremor, cerebellar tremor, psychogenic tremor, physiologic tremor, enhanced physiologic tremor, parkinsonian tremor, and orthostatic tremor.

8. The system of claim 1, wherein the control system is further configured to:

analyze the movement-based biomarker;

compute a probabilistic likeliness measure for the biomarker, determine, based on the analysis of the movement-based biomarker and the probabilistic likeliness measure, a health status of the user; and cause, based on the health status of the user, a notification to be presented.

9. The system of claim 1, wherein the control system generates the movement-based biomarker based on a machine learning algorithm.

10. The system of claim 1, wherein the tracking module is an augmented reality tracking module.

11. A system for generating a movement-based biomarker, the system comprising:

an imaging device configured to generate image data associated with a user; and a control system communicatively coupled to the imaging device, the control system configured to:

identify, using the image data, a feature of the user;

calculate, using the image data associated with the user, locations of the feature of the user over a period of time;

calculate, using the locations of the feature of the user over the period of time relative to a reference element present in the image data that is separate from the feature, a movement of the feature of the user, wherein the control system utilizes a tracking module configured to estimate micro-distance instability vectors for the movement, and wherein a built-in image stabilizer of the imaging device is disabled during generation of the image data; and generate, using the movement of the feature of the user, the movement-based biomarker.

12. The system of claim 11, wherein the feature of the user is associated with an eye of the user.

13. The system of claim 12, wherein the feature of the user is one or more of a center of a pupil of the eye of the user, a center of an iris of the eye of the user, and a precise facial landmark.

14. The system of claim 11, wherein the image data is reproducible as a series of visually readable images, and wherein the locations of the feature of the user are based on distances from the feature of the user to boundaries of the images, and wherein the locations are analyzed in a frequency domain to identify a dominant tremor frequency.

15. The system of claim 11, wherein the image data is reproducible as a series of visually readable images, and wherein the locations of the feature of the user are based on one of:

a distance from the feature of the user to a boundary of the images reproduced from the image data; and a distance from the feature of the user to a reference point on a head or face of the user.

16. The system of claim 11, further comprising an inertial sensor, wherein the control system further uses inertial measurements from the inertial sensor to determine the movement-based biomarker, and combines the inertial measurements with the calculated movement of the feature to bolster an accuracy of the movement-based biomarker.

17. The system of claim 11, wherein the movement-based biomarker is associated with a health status of the user.

18. The system of claim 17, wherein the health status of the user is one or more of essential tremor, dystonic tremor, cerebellar tremor, psychogenic tremor, physiologic tremor, enhanced physiologic tremor, parkinsonian tremor, and orthostatic tremor.

19. A system for generating a movement-based biomarker, the system comprising:

an imaging device configured to generate image data associated with a user, the image data being reproducible as a series of images; and a control system communicatively coupled to the imaging device, the control system configured to:

identify, in each image of the series of images, an eye of the user;

calculate, for each image of the series of images, a location of the eye of the user;

calculate, based on the location of the eye of the user relative to a facial landmark reference element in each image of the series of images, a movement of the eye of the user, wherein the control system utilizes a tracking module configured to estimate micro-distance instability vectors for the movement, and wherein a built-in image stabilizer of the imaging device is disabled during generation of the image data; and generate, based on the movement of the eye of the user, the movement-based biomarker.

20. The system of claim 19, wherein the eye of the user includes a first eye and a second eye, and wherein the location of the eye of the user includes a location of the first eye and a location of the second eye.

* * * * *